US00PP32859P2

(12) United States Plant Patent
Koot

(10) Patent No.: US PP32,859 P2
(45) Date of Patent: Mar. 2, 2021

(54) POINSETTIA PLANT NAMED 'DOPOINIMP'

(50) Latin Name: ***Euphorbia pulcherrima* Willd.**
Varietal Denomination: Dopoinimp

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,896

(22) Filed: Aug. 4, 2020

(51) Int. Cl.
*A01H 5/02* (2018.01)
*A01H 6/38* (2018.01)

(52) U.S. Cl.
USPC ..... Plt./307
CPC ..... *A01H 6/385* (2018.05)

(58) Field of Classification Search
USPC ..... Plt./307
CPC ..... A01H 6/385
See application file for complete search history.

(56) References Cited

PUBLICATIONS

UPOV hit on poinsettia plant named, 'Dopoinimp' QZ PBR 20200592, filed Feb. 26, 2020.*

* cited by examiner

*Primary Examiner* — Anne Marie Grunberg
(74) *Attorney, Agent, or Firm* — C. Anne Whealy

(57) ABSTRACT

A new and distinct cultivar of Poinsettia plant named 'Dopoinimp', characterized by its uniform, upright and mounded plant habit; moderately vigorous growth habit; freely and upright branching habit with strong lateral branches; dark green-colored leaves; plants typically flower in October and November under natural season conditions; large inflorescences with strong to vivid red-colored flower bracts; and good post-production longevity.

1 Drawing Sheet

Botanical designation: *Euphorbia pulcherrima* Willd.
Cultivar denomination: 'DOPOINIMP'.

CROSS-REFERENCE TO A RELATED APPLICATION AND STATEMENT REGARDING PRIOR DISCLOSURES BY INVENTOR AND APPLICANT

This application claims priority to a European Community Plant Breeders' Rights application filed on Feb. 26, 2020, application number 2020/0592. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of Poinsettia plant, botanically known as *Euphorbia pulcherrima* Willd., and hereinafter referred to by the cultivar name 'Dopoinimp'.

The new Poinsettia plant is a product of a planned breeding program conducted by the Inventor in Rheinberg, Germany. The objective of the breeding program is to create new uniform Poinsettia plants having large inflorescences with attractive flower bracts and excellent post-production longevity.

The new Poinsettia plant originated from a cross-pollination made by the Inventor in July, 2015 of a proprietary selection of *Euphorbia pulcherrima* Willd. identified as code number EE-0400, not patented, as the female, or seed, parent, with a proprietary selection of *Euphorbia pulcherrima* Willd. identified as code number EE12-522539-008, not patented, as the male, or pollen, parent. The new Poinsettia plant was discovered and selected by the Inventor as a single flowering plant from within the progeny of the stated cross-pollination in a controlled greenhouse environment in Rheinberg, Germany in December, 2019.

Asexual reproduction of the new Poinsettia plant by terminal vegetative cuttings in a controlled greenhouse environment in Rheinberg, Germany since January, 2020 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dopoinimp'. These characteristics in combination distinguish 'Dopoinimp' as a new and distinct Poinsettia plant:

1. Uniform, upright and mounded plant habit.
2. Moderately vigorous growth habit.
3. Freely and upright branching habit with strong lateral branches.
4. Dark green-colored leaves.
5. Under natural season conditions, plants typically flower in October and November.
6. Large inflorescences with strong and vivid red-colored flower bracts.
7. Good post-production longevity.

Plants of the new Poinsettia differ primarily from plants of the female parent selection in growth habit as plants of the new Poinsettia are more compact than and not as vigorous as plants of the female parent selection.

Plants of the new Poinsettia differ primarily from plants of the male parent selection in flowering habit as plants of the new Poinsettia flower later than plants of the male parent selection.

Plants of the new Poinsettia can be compared to plants of the *Euphorbia pulcherrima* Willd. 'Fiscor', disclosed in U.S. Plant Pat. No. 9,364. In side-by-side comparisons, plants of the new Poinsettia differ primarily from plants of 'Fiscor' in the following characteristics:

1. Plants of the new Poinsettia are larger than plants of 'Fiscor' with longer lateral branches and internodes.
2. Branching habit as plants of the new Poinsettia is more upright than branching habit of plants of 'Fiscor'.
3. Plants of the new Poinsettia have fewer cyathia per inflorescence than plants of 'Fiscor'.

BRIEF DESCRIPTION OF THE PHOTOGRAPH

The accompanying photograph illustrates the overall appearance of the new Poinsettia plant showing the colors as true as it is reasonably possible to obtain in colored reproductions of this type. Colors in the photograph may differ slightly from the color values cited in the detailed botanical description which accurately describe the colors of the new Poinsettia plant.

The photograph is a side perspective view of a typical flowering plant of 'Dopoinimp' grown in a container.

DETAILED BOTANICAL DESCRIPTION

Plants used in the aforementioned photograph and in the following detailed description were grown during the autumn and winter in 13-cm containers in a glass-covered greenhouse in Rheinberg, Germany under natural season conditions and cultural practices typical of commercial Poinsettia production. During the production of the plants, day and night temperatures averaged 18° C. and light levels averaged 4,500 lux. Plants were pinched one time about three weeks after planting rooted cuttings and were 23 weeks old when the photographs and the description were taken. Measurements and numerical values represent averages for typical flowering plants. In the following description, color references are made to The Royal Horticultural Society Colour Chart, 2015 Edition, except where general terms of ordinary dictionary significance are used.

Botanical classification: *Euphorbia pulcherrima* Willd. 'Dopoinimp'.

Parentage:

*Female, or seed, parent*.—Proprietary selection of *Euphorbia pulcherrima* Willd. identified as code number EE-0400, not patented.

*Male, or pollen, parent*.—Proprietary selection of *Euphorbia pulcherrima* Willd. identified as code number EE12-522539-008, not patented.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fibrous, fine; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Uniform, upright and mounded plant habit; inverted triangle; large inflorescences with numerous flower bracts positioned above the foliar plane; moderately vigorous growth habit.

*Plant height*.—About 26 cm.

*Plant diameter or spread*.—About 40 cm.

*Lateral branch description*.—Quantity: Freely branching habit with lateral branches potentially developing at every node after pinching; upright branching habit. Length: About 23 cm. Diameter: About 6 mm. Internode length: About 1.5 cm. Strength: Moderately strong. Texture: Smooth, glabrous. Luster: Moderately glossy. Color: Close to 137A.

*Leaf description*.—Arrangement: Alternate, simple. Length: About 14 cm. Width: About 8.3 cm. Shape: Ovate. Apex: Apiculate. Base: Obtuse. Margin: Irregularly lobed; slightly undulate. Aspect: Horizontal to drooping; keeled. Texture, upper surface: Smooth, glabrous. Texture, lower surface: Rugose, glabrous; prominent venation. Luster, upper and lower surfaces: Matte. Venation pattern: Pinnate, arcuate. Color: Developing leaves, upper surface: Close to 137A. Developing leaves, lower surface: Close to 138A. Fully developed leaves, upper surface: Close to 139A; venation, close to 146A. Fully developed leaves, lower surface: Close to 137A to 137B; venation, close to 146B to 146C. Leaf petioles: Length: About 4.9 cm. Diameter: About 3 mm. Texture, upper and lower surfaces: Smooth, glabrous. Luster, upper and lower surfaces: Matte. Color, upper surface: Close to 187A to 187B. Color, lower surface: Close to 187B to 187C.

Inflorescence description:

*Inflorescence type and habit*.—Terminal inflorescences are compound corymbs of cyathia with numerous colored flower bracts subtending the cyathia; inflorescences uniformly positioned above the foliar plane.

*Fragrance*.—None detected.

*Flowering response*.—Under natural season conditions, plants typically flower in October and November; under artificial long nyctoperiod/short photoperiod conditions, plants flower about eight weeks later.

*Post-production longevity*.—Good post-production longevity; plants of the new Poinsettia maintain good substance and flower bract color for about five to twelve weeks under interior conditions; flower bracts persistent and cyathia not persistent.

*Inflorescence diameter, without flower bracts*.—About 2 cm.

*Inflorescence height, without flower bracts*.—About 3.5 cm.

*Flower bracts*.—Quantity per inflorescence: Numerous, about eleven. Length, largest bracts: About 12.3 cm. Width, largest bracts: About 7.7 cm. Shape: Ovate. Apex: Apiculate. Base: Obtuse. Margin: Irregular lobing. Aspect: Flat, horizontal; keeled. Texture, upper surfaces: Smooth, glabrous. Texture, lower surface: Rugose, glabrous; prominent venation. Luster, upper and lower surfaces: Matte. Venation pattern: Pinnate, arcuate. Color: Developing bracts, upper surface: Close to 46A. Developing bracts, lower surface: Close to 53B. Developed bracts, upper surface: Close to 46A to 46B; color becoming closer to 46B to 46C with development. Developed bracts, lower surface: Close to 46A to 46B; color becoming closer to 46C to 46D. Bract petioles: Length: About 1.6 cm. Diameter: About 2 mm. Texture, upper and lower surfaces: Smooth, glabrous. Color, upper surface: Close to 53A. Color, lower surface: Close to 53B.

*Cyathia*.—Quantity per corymb: About five. Length: About 8 mm. Width: About 5 mm. Shape: Ovoid. Texture: Smooth, glabrous. Color: When developing, inner surface: Close to 143C. When developing, outer surface: Close to 143B. Fully developed, inner surface: Close to 143B. Fully developed, outer surface: Close to 143B to 143C.

*Nectaries*.—Quantity per cyathium: Typically two. Length: About 4 mm. Width: About 1 mm. Shape: Oval. Texture: Smooth, glabrous. Color: When developing and fully developed, inner surface: Close to 17A. When developing and fully developed, outer surface: Close to 17C.

*Peduncles*.—Length: About 4 mm. Diameter: About 1 mm. Strength: Strong. Aspect: Incurved. Texture: Smooth, glabrous. Color: Close to 143C.

*Reproductive organs*.—Stamens: Quantity per cyathium: About 20. Filament length: About 7 mm. Filament color: Close to 53A. Anther shape: Oval. Anther length: About 0.5 mm. Anther color: Close to 187A to 187B. Amount of pollen: Abundant. Pollen color: Close to 9A. Pistils: Quantity per cyathium: One; tri-parted. Pistil length: About 1 cm. Stigma shape: Crested. Stigma color: Close to 59A to 59B. Style length: About 2 mm. Style color: Close to 144B. Ovary color: Close to 144A. Fruits & seeds: To date, fruit and seed development has not been observed on plants of the new Poinsettia.

Pathogen & pest resistance: To date, plants of the new Poinsettia have not been shown to be resistant to pathogens and pests common to Poinsettia plants.

Temperature tolerance: Plants of the new Poinsettia have been observed to tolerate temperatures ranging from about 12° C. to about 40° C.

It is claimed:

1. A new and distinct Poinsettia plant named 'Dopoinimp' as illustrated and described.

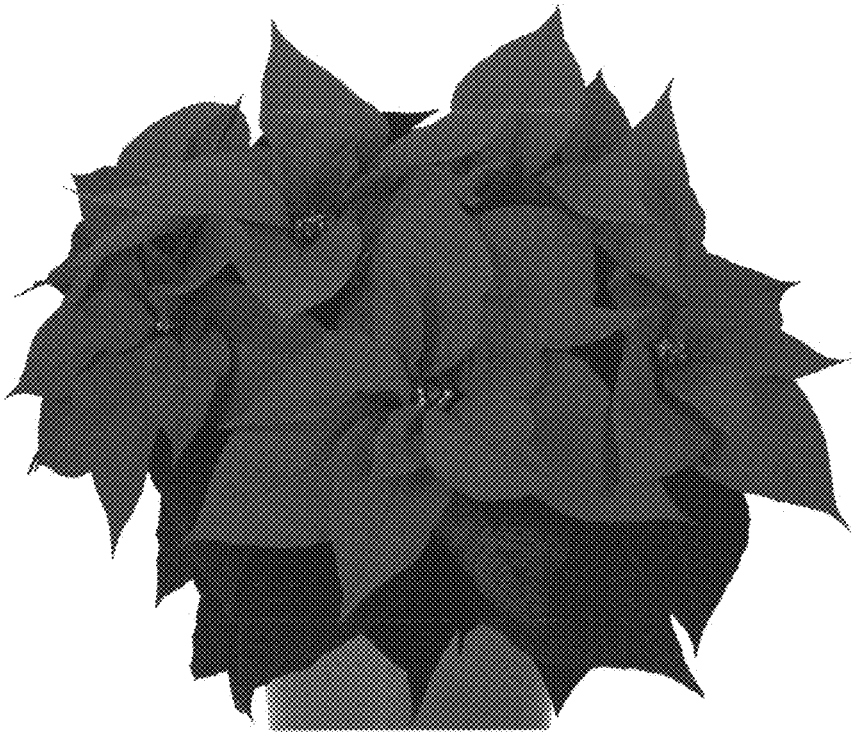

* * * * *